US009170193B2

United States Patent
Xu et al.

(10) Patent No.: US 9,170,193 B2
(45) Date of Patent: *Oct. 27, 2015

(54) DETECTING COOLANT LEAKS IN TURBINE GENERATORS

(71) Applicant: General Electric Company, Schenectady, NY (US)

(72) Inventors: James Jun Xu, Niskayuna, NY (US); Leonard Paul Squillacioti, Saratoga Springs, NY (US); Stephen Frank Francese, Malta, NY (US); Brian Scott Shewchuk, Marietta, GA (US); Erich John Wollman, Simpsonville, SC (US)

(73) Assignee: General Electric Company, Schenectady, NY (US)

( * ) Notice: Subject to any disclaimer, the term of this patent is extended or adjusted under 35 U.S.C. 154(b) by 145 days.

This patent is subject to a terminal disclaimer.

(21) Appl. No.: 13/911,567

(22) Filed: Jun. 6, 2013

(65) Prior Publication Data

US 2014/0362226 A1    Dec. 11, 2014

(51) Int. Cl.
  *G01N 21/3504*  (2014.01)
  *H04N 5/33*     (2006.01)
  *G01M 3/38*     (2006.01)
  *G01M 3/22*     (2006.01)

(52) U.S. Cl.
  CPC ........... *G01N 21/3504* (2013.01); *G01M 3/223* (2013.01); *G01M 3/228* (2013.01); *G01M 3/38* (2013.01); *H04N 5/33* (2013.01)

(58) Field of Classification Search
  CPC ....... G01N 21/3504; H04N 5/33; G01M 3/38; G01M 3/228; G01M 3/223
  See application file for complete search history.

(56) References Cited

U.S. PATENT DOCUMENTS

| 4,293,522 | A |   | 10/1981 | Winkler |
| 4,300,066 | A | * | 11/1981 | Butler, III ...................... 310/53 |
| 4,368,694 | A |   | 1/1983  | Ward et al. |
| 4,612,976 | A |   | 9/1986  | Soucille et al. |
| 4,724,799 | A |   | 2/1988  | Traiteur et al. |
| 4,755,473 | A |   | 7/1988  | Nishino et al. |
| 4,789,635 | A |   | 12/1988 | Ackland et al. |
| 4,790,327 | A |   | 12/1988 | Despotis |

(Continued)

FOREIGN PATENT DOCUMENTS

WO    WO 2010/049569 A1 *  5/2010

OTHER PUBLICATIONS

English translation copy obtained from WIPO of WO 2010/049569, May 6, 2010, 27 pages.*

(Continued)

*Primary Examiner* — David Porta
*Assistant Examiner* — Mindy Vu
(74) *Attorney, Agent, or Firm* — Ernest G. Cusick; Frank A. Landgraff

(57) ABSTRACT

An apparatus for detecting a leak in a gas cooled generator is provided. The apparatus includes a subsystem for introducing a non-corrosive second gas having an infrared absorption spectrum into the generator. The apparatus also includes an imaging component adapted to detect radiation at the infrared absorption spectrum of the non-corrosive second gas. The imaging component is provided with a filter that filters wavelengths in a range encompassing the infrared absorption spectrum of the non-corrosive second gas. The imaging component displays an image of the tracer gas leaking from the generator on the imaging component.

19 Claims, 4 Drawing Sheets

(56) References Cited

U.S. PATENT DOCUMENTS

| | | | |
|---|---|---|---|
| 4,801,551 A | 1/1989 | Byers et al. | |
| 4,822,336 A | 4/1989 | DiTraglia | |
| 4,830,010 A | 5/1989 | Marshall | |
| 4,851,088 A | 7/1989 | Chandrasekhar et al. | |
| 4,879,999 A | 11/1989 | Leiman et al. | |
| 4,945,918 A | 8/1990 | Abernathy | |
| 4,957,220 A | 9/1990 | Du | |
| 4,971,900 A | 11/1990 | Ahnell et al. | |
| 4,994,117 A | 2/1991 | Fehder | |
| 5,042,469 A | 8/1991 | Augustine | |
| 5,132,094 A | 7/1992 | Godec et al. | |
| 5,194,134 A | 3/1993 | Futata et al. | |
| 5,197,464 A | 3/1993 | Babb et al. | |
| 5,200,089 A | 4/1993 | Siefert et al. | |
| 5,203,320 A | 4/1993 | Augustine | |
| 5,235,846 A | 8/1993 | Fanciullo | |
| 5,272,087 A | 12/1993 | El Murr et al. | |
| 5,291,879 A | 3/1994 | Babb et al. | |
| 5,293,875 A | 3/1994 | Stone | |
| 5,320,967 A | 6/1994 | Avallone et al. | |
| 5,326,531 A | 7/1994 | Hahn et al. | |
| 5,335,536 A | 8/1994 | Runnevik | |
| 5,350,011 A | 9/1994 | Sylvester | |
| 5,357,971 A | 10/1994 | Sheehan et al. | |
| 5,399,535 A | 3/1995 | Whitman | |
| 5,404,885 A | 4/1995 | Sheehan et al. | |
| 5,432,061 A | 7/1995 | Berndt et al. | |
| 5,443,991 A | 8/1995 | Godec et al. | |
| 5,445,160 A | 8/1995 | Culver et al. | |
| 5,558,082 A | 9/1996 | Spencer | |
| 5,563,578 A | 10/1996 | Isenstein | |
| 5,565,619 A | 10/1996 | Thungstrom et al. | |
| 5,663,489 A | 9/1997 | Thungstrom et al. | |
| 5,749,358 A | 5/1998 | Good et al. | |
| 5,750,073 A | 5/1998 | Godec et al. | |
| 5,798,271 A | 8/1998 | Godec et al. | |
| 5,803,898 A | 9/1998 | Bashour | |
| 5,820,823 A | 10/1998 | Godec et al. | |
| 5,823,787 A | 10/1998 | Gonzalez et al. | |
| 5,846,836 A | 12/1998 | Mallow | |
| 5,857,460 A | 1/1999 | Popitz | |
| 5,859,503 A | 1/1999 | Potratz | |
| 5,867,105 A | 2/1999 | Hajel | |
| 5,902,751 A | 5/1999 | Godec et al. | |
| 5,924,995 A | 7/1999 | Klein et al. | |
| 5,932,791 A | 8/1999 | Hambitzer et al. | |
| 5,993,624 A | 11/1999 | Matsubara et al. | |
| 6,001,064 A | 12/1999 | Weckstrom | |
| 6,035,701 A * | 3/2000 | Lowry et al. | 73/40.7 |
| 6,058,933 A | 5/2000 | Good et al. | |
| 6,130,614 A | 10/2000 | Miller et al. | |
| 6,159,147 A | 12/2000 | Lichter et al. | |
| 6,164,277 A | 12/2000 | Merideth | |
| 6,183,695 B1 | 2/2001 | Godec et al. | |
| 6,190,327 B1 | 2/2001 | Isaacson et al. | |
| 6,228,325 B1 | 5/2001 | Godec et al. | |
| 6,247,470 B1 | 6/2001 | Ketchedjian | |
| 6,250,133 B1 | 6/2001 | Schell | |
| 6,318,296 B1 | 11/2001 | Nguyen | |
| 6,325,978 B1 | 12/2001 | Labuda et al. | |
| 6,365,022 B1 | 4/2002 | Hitchman et al. | |
| 6,378,517 B1 | 4/2002 | Steen | |
| 6,432,042 B1 | 8/2002 | Bashour | |
| 6,496,106 B1 | 12/2002 | Rodriguez | |
| 6,540,690 B1 | 4/2003 | Kanstad | |
| 6,544,190 B1 | 4/2003 | Smits et al. | |
| 6,584,974 B1 | 7/2003 | Ratner | |
| 6,586,173 B2 | 7/2003 | Tang | |
| 6,677,159 B1 | 1/2004 | Mallow | |
| 6,712,762 B1 | 3/2004 | Lichter et al. | |
| 6,723,285 B2 | 4/2004 | Chen et al. | |
| 6,736,199 B2 | 5/2004 | Wanni et al. | |
| 6,775,001 B2 | 8/2004 | Friberg et al. | |
| 6,780,646 B1 | 8/2004 | Brinton | |
| 6,786,182 B2 | 9/2004 | Morgandi et al. | |
| 6,874,502 B1 | 4/2005 | Nashed | |
| 6,923,939 B1 | 8/2005 | Nayar et al. | |
| 6,969,562 B2 | 11/2005 | Su et al. | |
| 6,990,980 B2 | 1/2006 | Richey, II | |
| 7,017,578 B2 | 3/2006 | Tresnak et al. | |
| 7,040,319 B1 | 5/2006 | Kelly et al. | |
| 7,098,012 B1 | 8/2006 | Szyf et al. | |
| 7,134,322 B1 * | 11/2006 | Baird | 73/40.7 |
| 7,140,370 B2 | 11/2006 | Tresnak et al. | |
| 7,142,105 B2 | 11/2006 | Chen | |
| 7,152,598 B2 | 12/2006 | Morris et al. | |
| 7,178,519 B2 | 2/2007 | Melker et al. | |
| 7,199,706 B2 | 4/2007 | Dawson et al. | |
| 7,229,832 B2 | 6/2007 | Nayar et al. | |
| 7,235,054 B2 | 6/2007 | Eckerbom | |
| 7,324,921 B2 | 1/2008 | Sugahara et al. | |
| 7,326,931 B2 | 2/2008 | Frodl et al. | |
| 7,335,164 B2 | 2/2008 | Mace et al. | |
| 7,344,503 B2 | 3/2008 | Friedman | |
| 7,353,691 B2 | 4/2008 | Salem et al. | |
| 7,361,946 B2 | 4/2008 | Johnson et al. | |
| 7,364,553 B2 | 4/2008 | Paz et al. | |
| 7,420,473 B2 | 9/2008 | Eicken et al. | |
| 7,445,602 B2 | 11/2008 | Yamamori et al. | |
| 7,455,644 B2 | 11/2008 | Yamamori et al. | |
| 7,464,040 B2 | 12/2008 | Joao | |
| 7,465,377 B2 | 12/2008 | Paris et al. | |
| 7,473,229 B2 | 1/2009 | Webber | |
| 7,490,048 B2 | 2/2009 | Joao | |
| 7,497,245 B2 | 3/2009 | Lorentz et al. | |
| 7,564,362 B2 | 7/2009 | Cole et al. | |
| 7,608,460 B2 | 10/2009 | Reed et al. | |
| 7,621,270 B2 | 11/2009 | Morris et al. | |
| 7,626,168 B2 | 12/2009 | Fischer et al. | |
| 7,666,377 B2 | 2/2010 | Wu et al. | |
| 7,675,655 B2 | 3/2010 | Marshall et al. | |
| 7,712,517 B2 | 5/2010 | Gandolfi et al. | |
| 7,723,711 B2 | 5/2010 | Schoo et al. | |
| 7,749,169 B2 | 7/2010 | Bayer et al. | |
| 7,805,256 B2 | 9/2010 | Frodl | |
| 7,811,276 B2 | 10/2010 | O'Neil et al. | |
| 7,811,433 B2 | 10/2010 | Manoukian et al. | |
| 7,833,480 B2 | 11/2010 | Blazewics et al. | |
| 7,839,290 B2 | 11/2010 | Chidakel et al. | |
| 7,842,925 B2 | 11/2010 | Straub et al. | |
| 7,897,109 B2 | 3/2011 | Labuda et al. | |
| 7,913,541 B2 | 3/2011 | Serban et al. | |
| 7,932,496 B2 | 4/2011 | Kato et al. | |
| 7,967,759 B2 | 6/2011 | Couvillon, Jr. | |
| 7,968,346 B2 | 6/2011 | Reed et al. | |
| 7,972,824 B2 | 7/2011 | Simpson et al. | |
| 7,992,561 B2 | 8/2011 | Baker, Jr. et al. | |
| 7,993,586 B2 | 8/2011 | Fujiyama et al. | |
| 7,997,408 B2 | 8/2011 | Peck | |
| 8,028,701 B2 | 10/2011 | Al-Ali et al. | |
| 8,062,221 B2 | 11/2011 | Debreczeny | |
| 8,066,004 B2 | 11/2011 | Morris et al. | |
| 8,083,684 B2 | 12/2011 | Palatnik | |
| 8,109,272 B2 | 2/2012 | Baker, Jr. et al. | |
| 8,124,419 B2 | 2/2012 | Brahim et al. | |
| 8,128,574 B2 | 3/2012 | Baker, Jr. et al. | |
| 8,148,167 B2 | 4/2012 | Reed et al. | |
| 8,166,967 B2 | 5/2012 | Qiu | |
| 8,183,052 B2 | 5/2012 | Reed et al. | |
| 8,188,485 B2 | 5/2012 | Schoo et al. | |
| 8,230,720 B2 | 7/2012 | Serban et al. | |
| 8,233,954 B2 | 7/2012 | Serban et al. | |
| 8,236,459 B2 | 8/2012 | Ha et al. | |
| 8,256,414 B2 | 9/2012 | Ratner | |
| 8,261,742 B2 | 9/2012 | Strothmann et al. | |
| 8,274,393 B2 | 9/2012 | Ales et al. | |

(56) References Cited

U.S. PATENT DOCUMENTS

| | | |
|---|---|---|
| 8,283,918 B2 | 10/2012 | Park et al. |
| 8,334,975 B1 | 12/2012 | Cook |
| 8,335,992 B2 | 12/2012 | Skidmore et al. |
| 2008/0231719 A1* | 9/2008 | Benson et al. ............. 348/222.1 |
| 2012/0330224 A1* | 12/2012 | Mailova et al. ................. 604/24 |

OTHER PUBLICATIONS

U.S. Appl. No. 13/948,400, filed Jul. 23, 2013, James Jun Xu.

Xu, J. and A Garton, "The Chemical Composition of Water Trees in EPR Cable Insulation, IEEE Transactions, Dielectrics and Electrical Insulation", Feb. 1994, 1, 18-24.

* cited by examiner

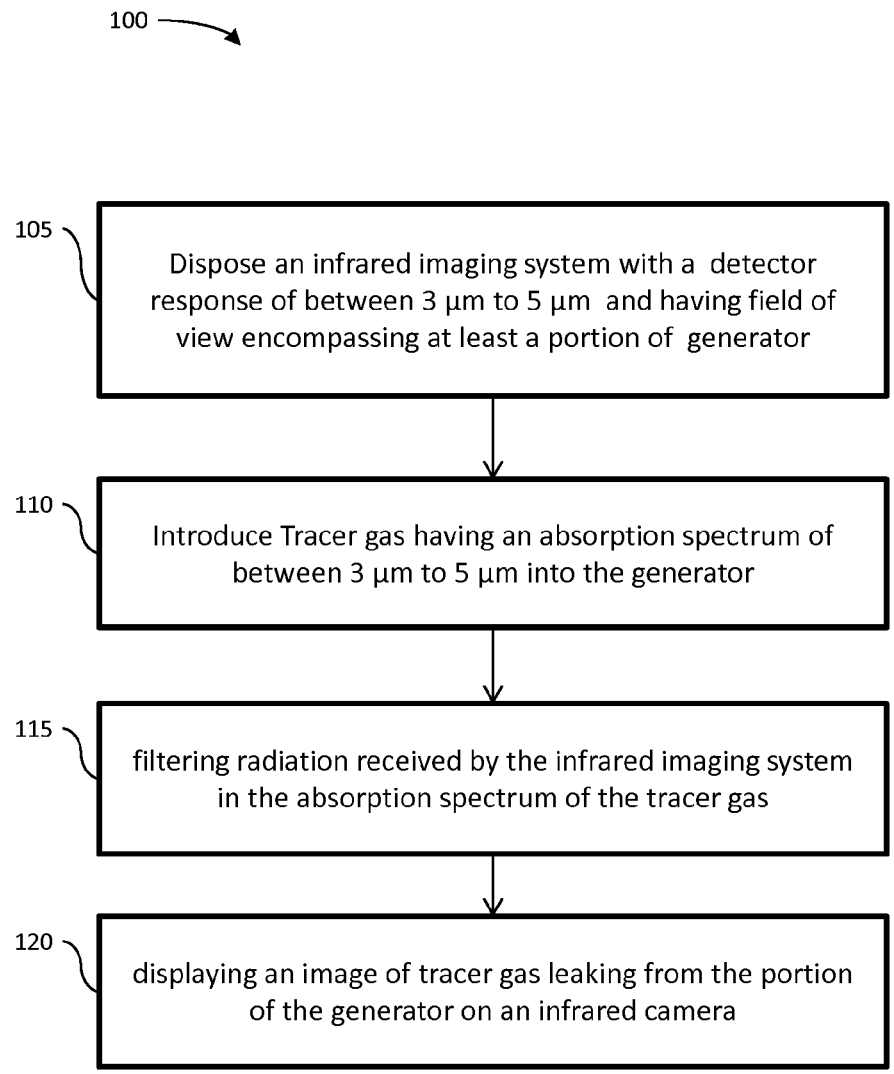

DETECTING COOLANT LEAKS IN TURBINE GENERATORS

TECHNICAL FIELD

The subject matter disclosed herein generally relates to detection of leaks and more particularly to the detection of coolant leaks in turbine generators.

BACKGROUND

Large turbine generators are typically cooled with a light density gas. Hydrogen ($H_2$) has been widely used as a coolant due to its desirable thermophysical properties including low windage friction, high heat dissipation capability and high resistance to corona discharge when compared to other cooling gas options. Additionally, $H_2$ has the advantage of being readily accessible and inexpensive.

Leakage of $H_2$ may prevent the turbine generator from operating efficiently, and in some cases may create power generation outages. Among possible areas of $H_2$ leakage around a turbine generator, are leaky spots at the wave stator casing including high voltage bushings and joints. Leaks may also occur around the interfaces of the cooler, welds, bolt heads and endshield. The bearing enclosure in the outer end shields, the rotor terminal packing, as well as drill holes made for instrumentation plug-ins may also be susceptible to leaks. Other air-tight transitions and welding joints may be sources of leaks, as well as the seal oil drain system, gas piping, and hydrogen cabinet. If the generator is a water cooled generator the stator liquid cooled windings also may be a source of leaks.

$H_2$ leaks are difficult to detect because $H_2$ is colorless and odorless, and because of its low density it dissipates quickly when it leaks into the atmosphere. The technical challenges in monitoring and detecting a potential $H_2$ leak lie in identifying the exact location of $H_2$ leaking in a turbine generator, especially in inaccessible and space limited areas.

Conventional turbine generator leak detection methods require the purging of the turbine generator with air and thereafter bringing it up to normal operating pressure. Then a long check list of areas to be examined and algorithm of step-by-step elimination are used. Each cycle of the testing requires monitoring for at least 24 hours. Standard formulae for volume, temperature and pressure are used to calculate loss of air over each period, and then a conversion is made to determine the equivalent $H_2$ loss. If the leakage is higher than recommended a variety of methods of leak detection have been used.

For example, a bubble test may be performed using soapy water or a similar detergent solution applied over all the accessible areas of possible leaks. If the leakage is inward in the stator liquid cooled windings, a flammable gas detector may even be used at the vent. The leak rate is determined by a "bag" test method. The process is time consuming because each time a leak is located in those accessible areas and repaired, another air test is required to confirm that the $H_2$ system is at an acceptable leakage rate. Each test cycle adds 24 hours to the outage.

Another approach is to use a halogen leak detector designed for detecting leaks in a pressurized system where halogen compound gases (such as Freon 12) are used as a tracer gas to check for leaks. The exterior of the system is then scanned with a sniffer probe sensitive to traces of the halogen-bearing gas. The principle is based on the increased positive ions (K or Na) emission because of sudden halide composition presence.

Yet another approach is to use a flammable gas detector designed to display a reading based on a percentage of the lower explosive limit of a hydrogen-air mixture (4% hydrogen in 100% air—therefore a 100% scale reading indicates a 4% or greater concentration of hydrogen in air).

Yet another approach is to use an ultrasonic leak detector that utilizes the ultrasonic energy generated by molecular collisions as gas escapes from or enters a small orifice. Pressurized gas proceeds from the leak locale and are detected with a sensitive microphone (typically about 40 000 Hz).

Multiple gas detectors have also been used. This type of leak detector is sensitive to a wide range of different gases in air. It detects inert gases (such as helium), flammable gases (hydrogen), corrosive gases (ammonia, chlorine), halogens (Freon) and also carbon dioxide.

Another approach has been to add odorants indicate the general area of the leak, after which the leak may be traced to its source by one of the foregoing methods.

All conventional methods of leak detection require the detector to be in close proximity to the source of the leak and take considerable time to implement. Most of the conventional methods use close or near contact "sniffer" technology and probes. These methods are painstakingly time consuming and in some cases miss the gas leaks. If the inaccessible $H_2$ sealing system or constrained space is the source of a possible leak, considerable effort to disassemble the turbine generator may be needed, commonly resulting in delaying the schedule several more days. Values approaching $1 MM loss of operating revenue per day have been reported by power producers when a turbine generator is off-line.

Long wave gas detection cameras (detector response of 10-11 µm) have been used in the electrical distribution industry to detect leakage of Sulfur Hexafluoride ($SF_6$) from high voltage switchgear and transformers. It has also been proposed to use $SF_6$ as a tracer gas in finding $H_2$ leaks in power plant generators in combination with backscatter/absorption technology. The backscatter/absorption leak detection process uses an active scanning laser to provide a directed energy source to irradiate a target area. The laser beam is reflected back to the source camera tuned to a specific frequency band. $SF_6$ has high affinity to absorb this frequency of energy and appear as a dark cloud on the camera monitor. The camera monitor provides a direct indication of how serious the leaks are by the size and darkness of the tracer gas cloud.

The major issues associated with the use of $SF_6$ as a tracer gas relate to environmental, health, and safety concerns and the potential deterioration of turbine generator insulation systems and retaining rings. $SF_6$ is a potent greenhouse gas with a 'global warming potential' (GWP) of 23,900 and an atmospheric lifetime of 3,200 years. The release of 1 kg of $SF_6$ into the atmosphere has the same impact as a release of 23,900 kg of $CO_2$. Release of $SF_6$ to the environment after detection, or the remaining residue at ppm (parts per million) level is of environmental, health, and safety concern. Additionally, in the presence of potential corona activities and thermal stress during turbine generator operations, $SF_6$ can decompose into harmful byproducts. These byproducts include HF, $SF_4$, $SO_2$, and $SO_2F_2$ which are toxic gases. In the presence of moisture, the primary and secondary decomposition products of $SF_6$ form corrosive electrolytes which may cause damage and operational failure to an $H_2$ cooled turbine generator. For example, $SF_6$ and its degradation byproduct have known corrosion effects on generator field retaining ring material whose main composition is 18Cr-18C stainless steel.

Existing methods do not provide a remote, sensitive, accurate, safe, fast and non-corrosive detection capability adaptable to being integrated with an on-line control system.

BRIEF DESCRIPTION OF THE INVENTION

The disclosure provides apparatuses, methods and systems for the remote, sensitive, accurate, safe, and fast detection of an $H_2$ leak from an $H_2$ cooled turbine generator that avoids health, environmental and safety concerns as well as avoiding corrosion of generator components.

In accordance with one exemplary non-limiting embodiment, the invention relates to an apparatus for detecting a leak in a generator cooled by a first gas. The apparatus includes a subsystem for introducing a non-corrosive second gas having an infrared absorption spectrum into the generator. The apparatus further includes an imaging component adapted to detect radiation at the infrared absorption spectrum of the non-corrosive second gas, the imaging component having a filter that filters wavelengths in a range encompassing the infrared absorption spectrum of the non-corrosive second gas.

In another embodiment, a system for detecting a gas leak in a hydrogen cooled generator is provided. The system includes a source of non-corrosive tracer gas and a subsystem for introducing the tracer gas into the hydrogen cooled generator. The system further includes an infrared imaging device adapted to display an image of the tracer gas.

In another embodiment, a method for detecting a leak of a coolant in a generator is provided. The method includes disposing an infrared imaging system having a detector with a response of between 3 µm to 5 µm, and with a field of view encompassing at least a portion of the generator. The method also includes the step of introducing a tracer gas having an absorption spectrum of between 3 µm and 5 µm into the generator. The method includes filtering radiation received by the infrared imaging system in the absorption spectrum of the tracer gas, and displaying an image of tracer gas leaking from the portion of the generator on an infrared imaging device.

BRIEF DESCRIPTION OF THE DRAWINGS

Other features and advantages of the present invention will be apparent from the following more detailed description of the preferred embodiment, taken in conjunction with the accompanying drawings which illustrate, by way of example, the principles of certain aspects of the invention.

FIG. 6 is a flow chart of a method for detecting a leak of a coolant in a turbine generator.

DETAILED DESCRIPTION OF THE INVENTION

Aspects of the present disclosure include a system for detecting a coolant leak in a turbine generator through the introduction of an environmentally safe non-corrosive tracer gas into the generator. An infrared imaging device adapted to display an image of the escaping tracer gas is provided.

Figure 1:
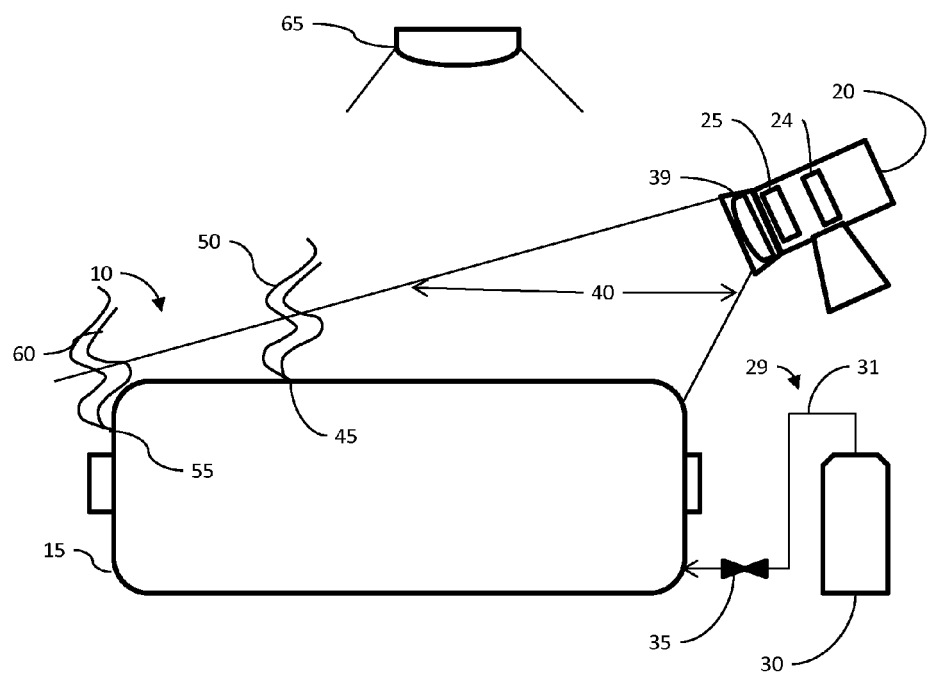
FIG. 1 is a schematic of an embodiment of a leak detection system.

Illustrated in FIG. 1 is a schematic of a leak detection system 10 for use in detecting leaks in an $H_2$ cooled turbine generator 15. The leak detection system 10 includes an infrared imaging device 20 capable of scanning large portions of the $H_2$ cooled turbine generator 15. The infrared imaging device 20 may be a portable, hand held, midwave infrared camera with a detector 24 having a response of 3 µm to 5 µm and may be further spectrally adapted to approximately 3.8 µm to 4.6 µm by use of a filter 25. The filter 25 restricts the wavelengths of radiation allowed to pass through to the detector 24 to a very narrow band called the band pass. This technique is called spectral adaptation. This makes the infrared imaging device 20 most responsive to gases that can be used as tracer gases.

The leak detection system 10 may include a subsystem for introducing a tracer gas 29, including a source of tracer gas 30 coupled to the $H_2$ cooled turbine generator 15 through conduit 31 and control valve 35. The infrared imaging device 20 may include an outer lens 39 that provides the infrared imaging device 20 with a field of view 40 encompassing a portion of the $H_2$ cooled turbine generator 15. If there is a leak point 45 on the $H_2$ cooled turbine generator 15 the leaking gas will generate a leak gas cloud 50 emanating from the leak point 45. Similarly, if there is a leak point 55 on the $H_2$ cooled turbine generator 15 the leaking gas will generate a leak gas cloud 60 emanating from the leak point 45. Leak gas cloud 50 and leak gas cloud 60 will contain tracer gas capable of being detected by the infrared imaging device 20.

In operation, the infrared imaging device 20 displays an image of the leak gas cloud 50 by rendering opaque the tracer gas in the leak gas cloud 50. For many gases, the ability to absorb infrared radiation depends on the wavelength of the radiation. In other words, their degree of transparency varies with wavelength. There may be infrared wavelengths where they are essentially opaque due to absorption. The infrared imaging device 20 is adapted to visualize the absorptive and emissive properties of tracer gases allowing the user the ability to discern the tracer gas from its host environment. The filter 25 is designed to transmit in an infrared spectrum that is coincident in wavelength with vibrational/rotational energy transitions of the molecular bonds of the tracer gas. These transitions are typically strongly coupled to the field via dipole moment changes in the molecule, and are common to many types of gases and vapors. The detector 24 of the infrared imaging device 20 may be cooled to 77° K. or approximately −196° C. in an Integrated Cooler Detector Assembly (IDCA), to increase the sensitivity of remote imaging of tracer gases. The thermal sensitivity is typically less than 20 mK, and more preferably less than 14 mK. The filter 25 may be mounted on the outer lens 39, or behind the outer lens 39, or inside IDCA assembly for increased versatility or sensitivity. The device may be calibrated and tuned with the largest contrast possible using modes of absorption, reflection or scattering so that the exact pressure, flow rate and temperature gradient of leaking tracer gas can be identified from varying detection distances.

If the infrared imaging device 20 is directed at an $H_2$ cooled turbine generator 15 without a gas leak, objects in the field of view will emit and reflect infrared radiation through the filter 25 of the infrared imaging device 20. The filter 25 will allow only certain wavelengths of radiation through to the detector 24 and from this the infrared imaging device 20 will generate an uncompensated image of radiation intensity. If there is a leak within the field of view 40 of the infrared imaging device 20 such as at leak point 45, a leak gas cloud 50 will be generated between the $H_2$ cooled turbine generator 15 and the infrared imaging device 20. The leak gas cloud 50 will contain tracer gas that absorbs radiation in the band pass range of the filter 25, and consequently the amount of radiation passing through the cloud and returning to the detector 24 will be reduced, thereby making the cloud visible through the infrared imaging device 20. If there is a leak outside of the field of view 40 of the infrared imaging device 20 such as at leak point 55, the portions of the leak gas cloud 60 would still be detected by the infrared imaging device 20. If desired, the corresponding level of $H_2$ can be estimated.

The tracer gas and its decomposition products, if any, should be environmentally safe from the point of view of toxicity and greenhouse effect. The tracer gas is preferably non-corrosive. Additionally, the tracer gas should not cause damage to generator insulation systems, or corrosive damage to steel retaining rings, and fan blades. Tracer gases may include hydrocarbon gases such as, for example Butane, Ethane, Heptane, Propane and the like. Preferably the tracer gas may be $CO_2$, which has unlimited mixing limits with both air and hydrogen. The background absorption of the $CO_2$ content of the atmosphere (400 ppm) may be eliminated when $CO_2$ is used as the tracer gas at concentrations greater than 400 ppm.

Figure 2:
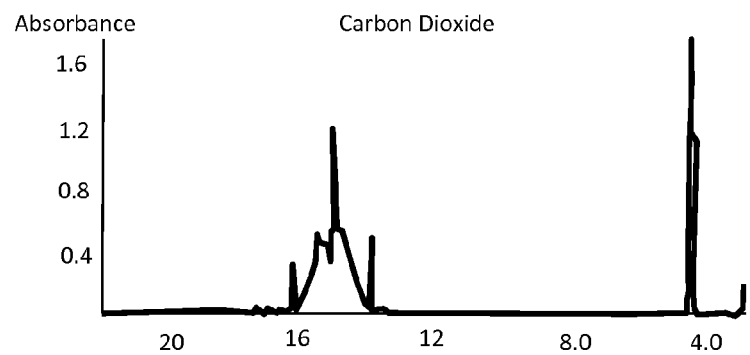
FIG. 2 is a chart of the absorption spectrum of $CO_2$.
Figure 3:
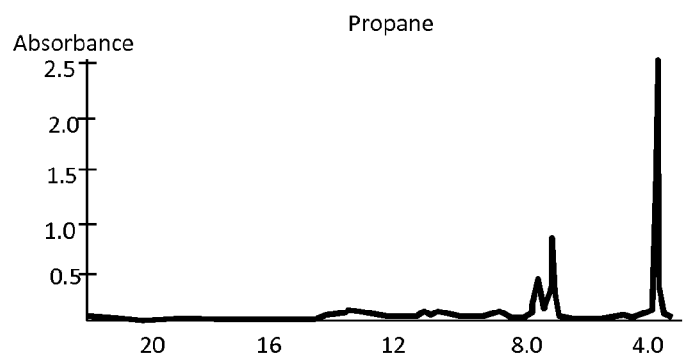
FIG. 3 is a chart of the absorption spectrum of Propane.
Figure 4:
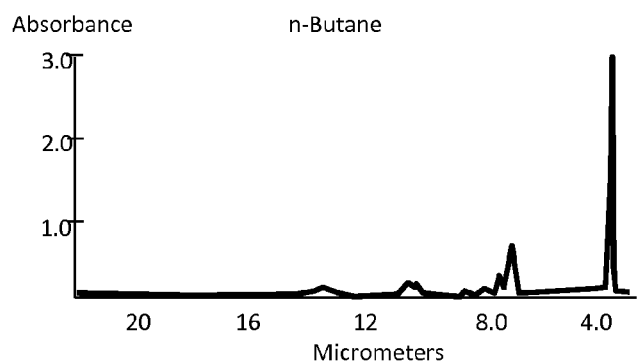
FIG. 4 is a chart of the absorption spectrum of n-Butane.

Illustrated in FIGS. 2, 3 and 4 are the absorption spectra of $CO_2$, propane and n-Butane respectively. As can be seen from the charts, $CO_2$, propane and n-Butane have a maximal absorption peak near 4 μm that can be detected with an infrared imaging device 20.

In one embodiment, detection of an $H_2$ leak may be performed while the $H_2$ cooled turbine generator 15 is in operation. The tracer gas may be introduced into the $H_2$ cooled turbine generator 15 from the bottom at the rate of about 24 liters per second, which corresponds to a rate of 4.7 liters/second per tracer gas cylinder. In this embodiment, the tracer gas may be up to 10% of the total generator coolant volume, or preferably up to 5% of the total generator coolant volume, or even more preferably up to 2% of the total generator coolant volume. The tracer gas is used to initially purge $H_2$ gas from the $H_2$ cooled turbine generator 15. In this embodiment, the tracer gas must have properties that allow for its use in an operating $H_2$ cooled turbine generator 15. Specifically, in this embodiment, the tracer gas preferably should not break down into corrosive components under the thermal stress and corona effects of the $H_2$ cooled turbine generator 15. The tracer gas in this embodiment should not cause unacceptable windage and thermal stresses in the components of the $H_2$ cooled turbine generator 15 such as the fan blade, field, stator core, and stator windings due to dilution of hydrogen purity. In operation the use of the tracer gas should not cause a temperature rise of more than 25° C. in the $H_2$ cooled turbine generator 15. A temperature rise of more than 25° C. is considered unacceptable in an operating $H_2$ cooled turbine generator 15. Most importantly, for non-$CO_2$ tracer gases, their lower and upper explosive limits with air need to be considered when used as tracer gases in an $H_2$ cooled turbine generator 15. The tracer gas should be compatible with any amount of $H_2$ in the $H_2$ cooled turbine generator 15 without causing combustion, or reacting with the $H_2$. The tracer gas should also have an appropriate density ranging from 0.5 to 2.5 g/liter so that it does not sink to the bottom of the $H_2$ cooled turbine generator 15. The stated density range avoids the possibility of missing leaks at the top of the $H_2$ cooled turbine generator 15 such as in bushing enclosures in lead-up units. High voltage bushings (not shown) are among the likeliest potential leak locations in $H_2$ sealing configurations in an $H_2$ cooled turbine generator 15.

In another embodiment, detection may be performed during scheduled outage shutdown procedure. When the leak detection is performed during a scheduled outage period, tracer gases other than $CO_2$ may be used, and cooling gas media other than $H_2$ may also be used. Tracer gases other than $CO_2$ should be compatible with the cooling gas media and oxygen containing media. The lower and upper flammable limits of non-$CO_2$ tracer gas with oxygen-containing media should be avoided. During a typical shutdown purging procedure for an $H_2$ cooled turbine generator 15, for instance, $H_2$ is replaced with $CO_2$ thereby purging the $H_2$ from the $H_2$ cooled turbine generator 15. Thereafter, air is used to purge the $CO_2$ from the $H_2$ cooled turbine generator 15. When the $H_2$ cooled turbine generator 15 is ready to be restarted, $CO_2$ is used to purge out the air, and then $H_2$ is used to purge out the $CO_2$. The periods where $CO_2$ is present in the $H_2$ cooled turbine generator 15 are the windows suitable for leak detection during a scheduled outage shutdown. In a typical shut down procedure, flow of the tracer gas into the $H_2$ cooled turbine generator 15 is controlled by means of a control valve 35. The gas content of the $H_2$ cooled turbine generator 15 may be pressurized. For example, the gas pressure in the $H_2$ cooled generator 15 may be maintained between 2-5 psig. Tracer gas (e.g. $CO_2$) is introduced into the $H_2$ cooled turbine generator 15. Although leak detection may start when the $CO_2$ content is anywhere between 1% and 100% it is preferable for leak detection to start when the $CO_2$ content is at least 70% and even more preferable when the $CO_2$ content is 100%. Even more preferable the leak detection may start when the $CO_2$ contents are pressurized up to 45 psig. The composition of the mixture of $H_2$ and tracer gas may be measured and monitored by a portable gas analyzer. The detection of the leak locations then may be started using the infrared imaging device 20. To return the $H_2$ cooled turbine generator 15 into operation the method starts with a similar procedure where more than 90% (by volume) of the tracer gas mixture is purged out by $H_2$ admitted from the top of the $H_2$ cooled turbine generator 15. During this procedure, the composition of the mixture of $H_2$ and tracer gas may be measured and monitored by a portable gas analyzer.

In yet another embodiment, the leak detection may be performed during the window when air is replacing $CO_2$ during the shutdown purging process of the $H_2$ cooled turbine generator 15. The leak detection may be performed when air reaches 1% to 99% (by volume) and remaining $CO_2$ is 99% to 1%. The air may be heated and pressurized up to 45 psig. Furthermore, the air may be heated prior to entering the $H_2$ cooled turbine generator 15. Air temperature of 3° C. or more preferably 5° C. or more above the ambient of any season may be preferred. The 1%-10% $CO_2$ may be detected readily since non-detectable limit of $CO_2$ is approximately 400 ppm (0.04% vol.).

In another embodiment a safe, non-corrosive, distantly detectable gas other than $H_2$ may be provided during the purging process. For example, $CO_2$ may be mixed not only with either $H_2$ and air during leak detection, but gases other than $H_2$ and air. These gases may include gases such as Nitrogen, Helium or Argon, etc. as a mixing media. Leak detection may be conducted when the content of $CO_2$ is between 1% and 100%.

Figure 5:
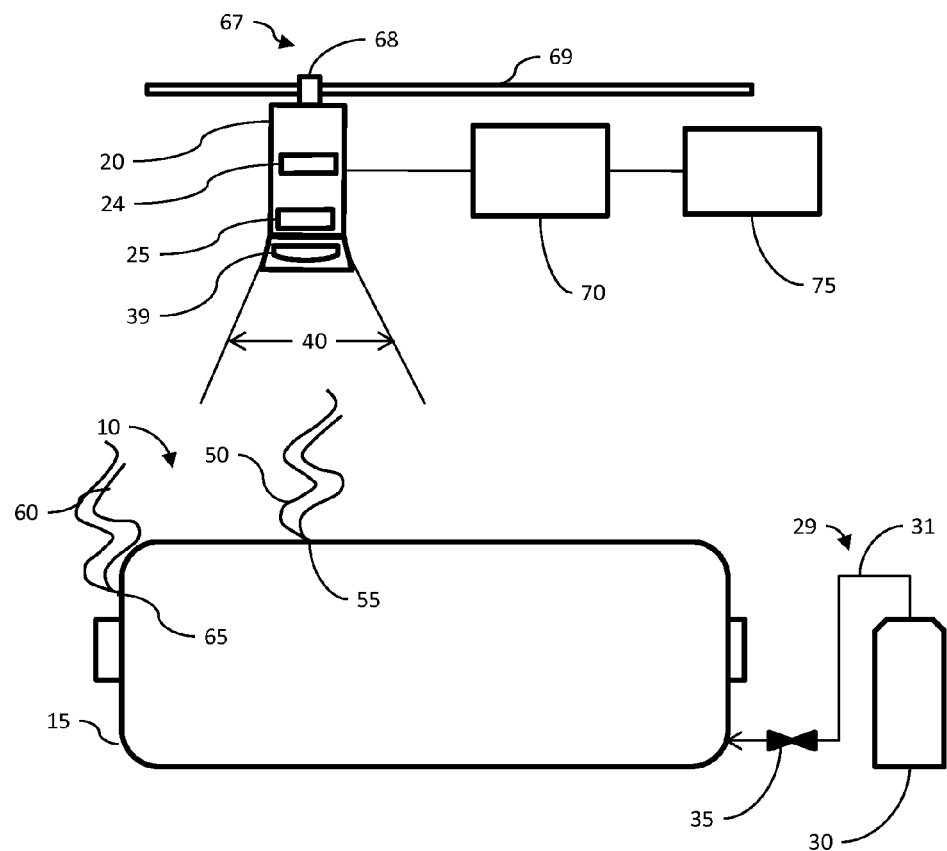
FIG. 5 is a schematic of an embodiment of a leak detection system.

As shown in FIG. 5, the infrared imaging device 20 may also be provided with a motorized subsystem 67 adapted to move the infrared imaging device 20 around the $H_2$ cooled turbine generator 15. The motorized subsystem 67 includes a rail 69 orbiting above or below the $H_2$ cooled turbine generator 15, and a motor 68 coupled to the infrared imaging device 20. The infrared imaging device 20 may be positioned so that the field of view 40 is disposed towards the $H_2$ cooled turbine generator 15 and its peripherals. The resulting image may be automatically transmitted to an image analyzer 70 coupled to a control system 75. The infrared imaging device 20 may be moved periodically or continuously to automatically detect leaks. The infrared imaging device 20 and image analyzer 70 may be separate or integrated units.

The infrared imaging device 20 may have a mountable 25 mm (~1 inch) outer lens 39 to enable focusing of the $H_2$ cooled turbine generator 15 from a distance of 10 feet to 50 feet. Distances of greater than 50 feet may require mounting a lens of 2 inches or more.

In yet another embodiment, the infrared imaging device 20 may be a thermographic infrared camera adapted to detect radiation in the infrared range of the electromagnetic spectrum (between 8 µm and 14 µm). Because the amount of radiation emitted by an object increases with temperature, an infrared imaging device 20 may be used to display variations in temperature. When viewed through a thermal imaging camera, warm objects stand out well against cooler backgrounds. The infrared imaging device 20 may be used to detect gas temperature that is at least 0.1° C. higher or lower, and preferably 1° C. or ° F. higher or lower, or even more preferably, 2-5° C. or ° F. higher or lower than that of atmosphere surrounding the $H_2$ cooled turbine generator 15 of interest. The infrared imaging device 20 may be used in a passive thermography system where the leak gas cloud 50 is at a higher or lower temperature than the background. Alternately the infrared imaging device 20 may be used as part of an active thermography system that utilizes an energy source to produce a thermal contrast between the leak gas cloud 50 and the background. In the latter case an infrared heating light 65 (shown in FIGS. 1 and 5) may be used to heat the local atmosphere of suspicious leak locales in order to create contrast with a leak gas cloud 50 escaping from a leak point 45. The distance, response time, angle of detection and image resolution may vary as required for the preferred temperature gradient of the leaking gas.

FIG. 6 is a flow chart of a method 100 for detecting a leak of coolant in an $H_2$ cooled turbine generator 15.

In step 105 an infrared imaging system is disposed with a field of view encompassing at least a portion of the $H_2$ cooled turbine generator 15.

In step 110 a tracer gas is introduced into the $H_2$ cooled turbine generator 15. The tracer gas will preferably have an absorption spectrum between 3 µm to 5 µm and more preferably between 3.9 µm to 4.6 µm. The tracer gas may be introduced from the bottom of the $H_2$ cooled turbine generator 15 to displace at least a portion of the coolant with the tracer gas. The tracer gas may have a density of between 0.5 to 2.5 g/liter. The tracer gas may be $CO_2$ and may be introduced into the $H_2$ cooled turbine generator 15 until the $CO_2$ content reaches a 1% to 100% level before leak detection is commenced. Leak detection may start when the $CO_2$ content has reached 1%. Preferably, leak detection is started when the $CO_2$ content reaches 70%, and even more preferable when the $CO_2$ content reaches 100%. Even more preferable, leak detection is started when the pressure of the $CO_2$ is approximately 45 psig. The tracer gas may be pressurized in the $H_2$ cooled turbine generator 15 up to 45 psig but below 75 psig when there is a need to identify the smallest leak locales. Although the method is described with $CO_2$ replacing $H_2$, it would be apparent to one of ordinary skill in the art that leak detection may be performed using CO2 in other gases as gas media. Such other gases may include air, Helium, Argon, Nitrogen and the like.

In step 115 the radiation received by the infrared imaging system is filtered in the absorption spectrum of the tracer gas.

In step 120 an image of the tracer gas leaking from the portion of the $H_2$ cooled turbine generator 15 is displayed on an infrared imaging device 20.

The embodiments set forth above do not exclude the use of a combination of leak detection methods. For instance, for the locales of notoriously known having high propensity of leak, an initial assessment can be made using an $H_2$ sniffing sensor. If a leak is detected, the location of the leak may be marked and thereafter the infrared imaging method disclosed herein may be used to detect additional leaks.

Where the definition of terms departs from the commonly used meaning of the term, applicant intends to utilize the definitions provided below, unless specifically indicated.

The terminology used herein is for the purpose of describing particular embodiments only and is not intended to be limiting of the invention. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). Where the definition of terms departs from the commonly used meaning of the term, applicant intends to utilize the definitions provided herein, unless specifically indicated. The singular forms "a", "an" and "the" are intended to include the plural forms as well, unless the context clearly indicates otherwise. It will be understood that, although the terms first, second, etc. may be used to describe various elements, these elements should not be limited by these terms. These terms are only used to distinguish one element from another. The term "and/or" includes any, and all, combinations of one or more of the associated listed items. The phrases "coupled to" and "coupled with" contemplates direct or indirect coupling.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements.

What is claimed:

1. An apparatus for detecting a leak in a generator cooled by a first gas, the apparatus comprising:

a subsystem for introducing a non-corrosive second gas having an infrared absorption spectrum into the generator, the non-corrosive second gas comprising an inert gas, and the subsystem further enables replacing the first gas with the inert gas and thereafter introducing air at a predetermined temperature until the inert gas is reduced to between 99% to 1% by volume; and an imaging component adapted to detect radiation at the infrared absorption spectrum of the non-corrosive second gas, the imaging component having a filter that filters wavelengths in a range encompassing the infrared absorption spectrum of the non-corrosive second gas.

2. The apparatus of claim 1, wherein the imaging component comprises an infrared imaging device with a cooled detector having a spectral response between 3 µm and 5 µm.

3. The apparatus of claim 2, wherein the filter narrows a cooled detector response of the infrared imaging device to between 3.9 µm and 4.6 µm.

4. The apparatus of claim 2, further comprising an imaging device subsystem that moves the infrared imaging device around the generator.

5. The apparatus of claim 1, wherein the non-corrosive second gas has an absorption spectrum of between 3.8 µm and 4.6 µm.

6. The apparatus of claim 1, wherein the non-corrosive second gas is a non-corrosive second gas selected from among a group comprising hydrocarbons and carbon dioxide.

7. The apparatus of claim 1, wherein the subsystem for introducing a non-corrosive second gas comprises:
a source of the non-corrosive second gas; and
a control valve.

8. A system for detecting a gas leak in a hydrogen cooled generator, the system comprising:
a source of non-corrosive tracer gas;
a subsystem for introducing non-corrosive tracer gas into the hydrogen cooled generator, the non-corrosive second gas comprising an inert gas, and the subsystem further enables replacing the hydrogen with the inert gas and thereafter introducing air at a predetermined temperature until the inert gas is reduced to between 99% to 1% by volume; and
an infrared imaging device adapted to display an image of the non-corrosive tracer gas.

9. The system of claim 8, wherein the source of non-corrosive tracer gas is a source of hydrocarbon gas.

10. The system of claim 8, wherein the source of non-corrosive tracer gas is a source of carbon dioxide.

11. The system of claim 8, wherein the infrared imaging device is a passive infrared imaging system.

12. The system of claim 8, wherein the infrared imaging device is a manually operated active infrared imaging system.

13. The system of claim 8, further comprising an imaging device subsystem that moves the infrared imaging device around the hydrogen cooled generator.

14. The system of claim 8, wherein the infrared imaging device comprises a filter.

15. A method for detecting a leak of a coolant in a generator, the method comprising:
disposing an infrared imaging device having a cooled detector response of between 3 μm to 5 μm with a field of view encompassing at least a portion of the generator;
introducing a tracer gas into the generator the tracer gas having an absorption spectrum of between 3 μm and 5 μm;
filtering radiation received by the infrared imaging device in the absorption spectrum of the tracer gas;
displaying an image of tracer gas leaking from the portion of the generator on the infrared imaging device, wherein the step of introducing the tracer gas comprises replacing the coolant with carbon dioxide, and thereafter introducing air at a predetermined temperature until the carbon dioxide is reduced to between 99% to 1% by volume.

16. The method of claim 15, wherein the step of introducing a tracer gas comprises introducing the tracer gas from the bottom of the generator.

17. The method of claim 15, wherein the tracer gas has a density of between 0.5 to 2.5 igniter.

18. The method of claim 15, wherein the tracer gas has an absorption spectrum of between 3.9 μm to 4.6 μm.

19. The method of claim 15, wherein the step of introducing the tracer gas comprises introducing carbon dioxide until the carbon dioxide reaches approximately between 1% to 100% by volume.

\* \* \* \* \*